United States Patent [19]
Katsoulis et al.

[11] Patent Number: 5,179,220

[45] Date of Patent: Jan. 12, 1993

[54] NON-AQUEOUS SOLUTIONS OF ALUMINUM AND ALUMINUM-ZIRCONIUM COMPOUNDS

[75] Inventors: Dimitris E. Katsoulis; Donald A. Kadlec, both of Midland, Mich.

[73] Assignee: Somerville Technology Group, Inc., Huguenot, N.Y.

[21] Appl. No.: 724,302

[22] Filed: Jul. 1, 1991

[51] Int. Cl.$^5$ .................. A61K 7/34; A61K 7/38; C07F 5/06; C07F 9/00
[52] U.S. Cl. .................. 556/27; 424/DIG. 5; 424/47; 424/66; 424/68; 556/181
[58] Field of Search .................. 556/181, 27; 424/66, 424/68

[56] References Cited

U.S. PATENT DOCUMENTS

| | | | |
|---|---|---|---|
| 3,256,188 | 6/1966 | Papayannopoulos et al. | 556/181 |
| 3,290,349 | 12/1966 | Lundeen et al. | 556/181 |
| 3,359,169 | 12/1967 | Slater | 167/90 |
| 3,405,153 | 10/1968 | Jones | 260/429.3 |
| 3,420,932 | 1/1969 | Jones | 424/47 |
| 3,472,929 | 10/1969 | Jones | 424/68 |
| 3,507,896 | 4/1970 | Jones | 260/448 |
| 3,509,253 | 4/1970 | Babbin | 424/47 |
| 3,523,130 | 4/1970 | Jones | 260/448 |
| 3,523,153 | 8/1970 | Holbert | 424/47 |
| 3,638,327 | 2/1972 | Levy | 34/5 |
| 3,876,758 | 4/1975 | Beekman | 424/47 |
| 3,904,741 | 10/1975 | Jones | 423/462 |
| 3,947,556 | 3/1976 | Jones | 423/463 |
| 4,025,615 | 5/1977 | Rubino | 424/67 |

FOREIGN PATENT DOCUMENTS 0007191  6/1979  European Pat. Off. ............. 424/68

*Primary Examiner*—Dale R. Ore
*Attorney, Agent, or Firm*—Kenneth P. Glynn

[57] ABSTRACT

This invention pertains to a method of making non-aqueous solutions of aluminum and aluminum-zirconium compounds. The non-aqueous solutions are produced by: (A) protonating a hydroxylated solvent, such as ethanol or propylene glycol, by adding an acid selected from $ZrOCl_2$, $ZrO(OH)Cl$, $ZrCl_4$, $AlCl_3$, HCl, HI, HBr, $HNO_3$, and mixtures thereof to the hydroxylated solvent; and (B) adding at a controlled rate to protonated solvent aluminum chlorohydrate, $Al_2(OH)_aCl_{6-a}$, wherein a has the value of greater than 0 but less than 6; until the desired solution is formed. The non-aqueous solutions are useful in antiperspirant compositions.

14 Claims, No Drawings

NON-AQUEOUS SOLUTIONS OF ALUMINUM AND ALUMINUM-ZIRCONIUM COMPOUNDS

BACKGROUND OF THE INVENTION

Traditional aluminum halohydrate and aluminum-zirconium-glycine halohydrate salts are soluble only in aqueous solutions. The only alcohol soluble materials that have been prepared so far are aluminum halohydrate compounds that contain very high excess of chloride (Al:Cl~1.3), and a controlled moisture content. The high acid condition make these compounds more irritating than the regular antiperspirant products (which have an Al:Cl~2), and the high moisture content calls for very specific spray drying conditions that make the manufacturing of these products a rather delicate matter.

Alcohol or other non-aqueous solutions of aluminum-zirconium-glycine halohydrates salts are not well known in the art. This is because glycine is typically not soluble in the non-aqueous medium and methods for producing solid aluminum-zirconium halohydrates (without glycine) is not known in the art.

U.S. Pat. No. 3,359,169 to Slater et al., teaches a method for reacting aluminum and aluminum chlorohydroxides with hydroxylic organic compounds. The aluminum and aluminum chlorohydroxides are produced by contacting an aluminum compound with a hydroxylic reagent in the presence of sufficient water to dissolve the aluminum compound and then removing water from the system by evaporation. The compound prepared by the method taught by Slater et al. have a high degree of solubility in ethyl alcohol and glycols.

U.S. Pat. No. 3,405,153 to Jones et al., teaches a method of making novel metal-aluminum inorganic-organic complexes which are significantly soluble in non-aqueous media. The method comprises (A) mixing an aqueous solution of an aluminum-containing material with a zinc halide or zirconyl halide; (B) adding to that mixture a polyhydroxy compound having at least 2 carbon atoms, each of which is linked to a hydroxy group; (C) heating the mixture to a temperature of from about 50° C. to about 120° C. to evaporate moisture to about 0.8 of original volume; and (D) drying the heated mixture until a constant weight is achieved and the product has a moisture content of from about 0.5 to about 20%. The resulting salts are soluble in non-aqueous solvents, for example ethanol, in concentrations of at least 10%.

U.S. Pat. No. 3,420,932 to Jones et al., teaches a method of making inorganic-organic coordinated complex of aluminum. The method comprises making an aqueous solution of aluminum chloride and aluminum bromide, mixing the solution with a polyhydroxy compound, heating the mixture and spray drying the mixture to obtain a product having a water content of about 1.0 to 10 weight percent. The inorganic-organic complexes are significantly soluble in non-aqueous medium.

U.S. Pat. No. 3,472,929 to Jones et al. teaches a method of making alcohol-soluble complexes of aluminum which consists of reacting a basic aluminum chloride and a polyhydroxy compound in an ethanol-water solution and distilling off the ethanol and water to a product which has 0.2 to 3.0 weight percent water. This invention produces alcohol soluble aluminum salts without the need for spray drying.

U.S. Pat. No. 3,507,896 to Jones et al., teaches a method of making alcohol soluble salts by reacting aluminum powder, a polyhydroxy compound and an acid in water, filtering the mixture and then drying the filtrate to remove water to form a product having from about 1.0 to 10 weight percent water.

U.S. Pat. No. 3,509,253 to Babbin, teaches an alcohol soluble complex of aluminum chloride. The complex is produced by reacting aluminum chloride or aluminum chlorhydroxide with an alcohol in an aqueous solution. The water is then removed by evaporation, crystallization or other means.

U.S. Pat. No. 3,523,130 to Jones et al., teaches a method of preparing inorganic-organic coordinated complex of aluminum comprising refluxing an aqueous solution of basic aluminum chloride and then reacting the refluxed aluminum chloride with a polyhydroxy compound and finally spray drying the reaction product to obtain a product having a water content of from 1.0 to 10 weight percent.

U.S. Pat. No. 3,523,153 to Holbert et al., teaches trichloro hydroxy aluminum derivatives in aerosol antiperspirant compositions. The trichloro hydroxy aluminum derivatives are produced by reacting aluminum chloride hexahydrate (dissolved in ethanol) with aluminum isoproplylate and recovering the reaction product produced.

U.S. Pat. No. 3,638,327 to Levy et al., teaches a method for making alcohol soluble aluminum chlorhydroxides by freeze drying the aluminum chlorhydroxide from an aqueous solution.

U.S. Pat. No. 3,876,758 to Beekman et al., teaches a method of making alcohol solutions of aluminum chlorhy-droxides for antiperspirant use. The process comprises reaction of a solution of aluminum chloride in an aliphatic alcohol with an aluminum chlorhydroxide-polyol composition. The aluminum chlorhydroxide polyol compositions are those taught in U.S. Pat. No. 3,359,169 to Slater et al.

U.S. Pat. No. 3,904,741 to Jones et al., teaches a method for the preparation of alcohol soluble basic aluminum chlorides. The method comprises controlling the molar ratio of aluminum to chloride and the amount of free and coordinated water in the solid. A preferred method is to heat an aluminum chloride solution having an Al:Cl ratio of about 1.9 under reflux for 2–4 hours and spray drying the solution to a friable solid having 18 to 20 weight percent of calculated free and coordinated water.

U.S. Pat. No. 3,947,556 to Jones et al., teaches a method for the preparation of alcohol soluble complexes of basic aluminum chlorides. The method comprises adding five-sixths basic aluminum chloride to a zinc halide or zirconyl bromide and drying the mixture to a substantially friable solid. The resulting solid contains about 12 to 30 weight percent water, are soluble in anhydrous alcohol and are compatible with halogenated hydrocarbons.

EP Patent Application No. 0007191 to Goslins et al. teaches a method of making aluminum chloride/polyhydroxide compound complexes by dissolving aluminum chlorhydrate and a polyhydroxide in water, heating the mixture and spray drying to a powder.

Most of the methods known in the art require the formation of the aluminum salt in an aqueous or aqueous/alcoholic medium, drying of the salt and then dissolving the salt in the alcoholic medium. These processes are inefficient because they require extreme control to ensure that the resulting salt is soluble in the alcoholic medium. Further, they have limited capability for producing alcoholic or other non-aqueous solutions of aluminum-zirconium halohydrates.

It is an object of the instant invention to show a method of producing non-aqueous solutions of aluminum and aluminum-zirconium compounds wherein the aluminum or aluminum-zirconium compound is formed "in-situ" in the non-aqueous solution.

SUMMARY OF THE INVENTION

The instant invention pertains to a method of making non-aqueous solutions of aluminum or aluminum-zirconium compounds by (1) protonating a hydroxylated solvent by adding an acid selected from $ZrOCl_2$, $ZrO(OH)Cl$, $ZrCl_4$, $AlCl_3$, $HCl$, $HI$, $HBr$, $HNO_3$, and mixtures thereof to the hydroxylated solvent; and (2) adding at a controlled rate to the protonated solvent aluminum chlorohydrate, $Al_2(OH)_aCl_{6-a}$, wherein a has the value of greater than 0 but less than 6, until the desired salt in the solution is formed. Heat may optionally be added at any step in the process. The resulting product is an aluminum or aluminum-zirconium compound which is dissolved in a non-aqueous medium.

THE INVENTION

The instant invention comprises a method wherein an aluminum or aluminum-zirconium compound is formed in-situ in a non-aqueous medium. The aluminum compounds produced by the method of this invention have the formula $$Al_w(OH)_x(R)_yX_z \cdot n(H_2O) \cdot p(R')$$

wherein R is selected from the anionic portion of the hydroxylated solvent; R' is the hydroxylated solvent; X is selected from Cl, Br, I, and $NO_3$, v/z has the value of 0.33 to 2; $x+y+z=6$; n is greater than 1; and p is greater than 1.

The aluminum-zirconium compounds produced by the method of this invention have the formula $$Al_bZr_c(OH)_d(R)_eX_f \cdot n(H_2O) \cdot p(R')$$

wherein R and R' are as described above; X is selected from Cl, Br, I, and $NO_3$, b/f has the value of 0.33 to 2; b/c has the value of at least 0.75; $3b+4c=d+e+f$; n is greater than 1; and p is greater than 1.

The method for producing non-aqueous solutions of aluminum and aluminum-zirconium compounds comprises (1) protonating a hydroxylated solvent by adding an acid selected from $ZrOCl_2$, $ZrO(OH)Cl$, $ZrCl_4$, $AlCl_3$, $HCl$, $HI$, $HBr$, $HNO_3$, and mixtures thereof to the hydroxylated solvent; and (2) adding at a controlled rate to protonated solvent aluminum chlorohydrate, $Al_2(OH)_aCl_{6-a}$, wherein a has the value of greater than 0 and less than 6; until the desired aluminum or aluminum-zirconium compound is formed.

The first step in the process of preparing non-aqueous solutions of aluminum and aluminum-zirconium compounds comprises adding an acid selected from $ZrOCl_2$, $ZrO(OH)Cl$, $ZrCl_4$, $AlCl_3$, $HCl$, $HBr$, $HI$, $HNO_3$, and mixtures thereof to a hydroxylated solvent. $AlCl_3$, $ZrOCl_2$, $ZrO(OH)Cl$, $HCl$ or mixtures thereof are the preferred acids to add to the hydroxylated solvent. When producing non-aqueous solutions of aluminum compounds it is preferred to use $AlCl_3$, $HCl$ and mixtures thereof as the acid. When producing non-aqueous aluminum-zirconium compounds it is preferred to use $AlCl_3$, $ZrOCl_2$, $ZrO(OH)Cl$, $HCl$ and mixtures thereof as the acid.

The solvent is protonated upon the addition of the acid. To ensure that this occurs, it may be necessary to apply heat to the solution. If heat is applied, it is preferred that temperatures less than 80° C. should be used at atmospheric pressure. The need for heat will depend on the hydroxylated solvent being employed and the amount and type of acid being added. For example, when adding $AlCl_3$ to ethanol it is almost always necessary to heat the solution. Further, when high concentrations of acid are being added, heat is typically required.

The amount of acid used to protonate the hydroxylated solvent will depend on the aluminum or aluminum-zirconium composition in the final solution and the solubility of the acid in the hydroxylated solvent. Typically 0.1 to 50 weight percent (based on the solvent weight) of acid is added into the hydroxylated solvent. One skilled in the art will readily be able to determine the amount of acid needed to produce the desired final composition.

Although the acid may be added to the hydroxylated solvent as an aqueous solution it is preferred that the acid be essentially free of water. It is further preferred that the acid be anhydrous. However, the acid may contain bound or free water.

Following the addition of the acid, aluminum chlorohydrate, $Al_2(OH)_aCl_{6-a}$, wherein a has the value of greater than 0 but less than 6, is added at a controlled rate while mixing. The aluminum chlorohydrates useful in the instant invention may be a standard (unactivated) or an activated aluminum chlorohydrate. An activated aluminum chlorohydrate is an aluminum chlorohydrate that has a higher efficacy and it typically comprised of a higher amount of one of the polymeric species of aluminum chlorohydrate known in the art as $Al_{13}$ or Band III.

The amount of aluminum chlorohydrate added is again dependent upon the desired aluminum or aluminum-zirconium composition in the non-aqueous solution and the solubility of the aluminum chlorohydrate in the protonated solvent. Typically 0.1 to 80 weight percent (based on the protonated solvent) of aluminum chlorohydrate is added into the protonated solvent solution. One skilled in the art will readily be able to determine the amount of aluminum chlorohydrate needed to produce the desired final composition.

Heat may optionally applied during the addition of the aluminum chlorohydrate. When heat is applied it is preferred that the solution be at a temperature of 40° C. to 80° C. during the addition of the aluminum chlorohydrate. The need for heat will depend on the hydroxylated solvent being employed and the desired solids level being produced. For example, when ethanol is the hydroxylated solvent it is almost always necessary to heat the solution. However, when propylene glycol is the hydroxylated solvent heat is typically not required but heat may optionally be added. Further, heat is typically required when there are higher levels of solids in the resulting solutions. One skilled in the art will be able to determine when heat is necessary during the addition of the aluminum chlorohydrate.

Additional acid, selected from $ZrOCl_2$, $ZrO(OH)Cl$, $ZrCl_4$, $AlCl_3$, $HCl$, $HI$, $HBr$, $HNO_3$, and mixtures thereof may be added with or following the addition of the aluminum chlorohydrate.

By varying the amount of acid and aluminum chlorohydrate added into the non-aqueous medium, solutions which contain different theoretical solids levels, aluminum:zirconium (Al:Zr) ratios and metals:halide (M:X) ratios can be produced.

The non-aqueous solutions of the aluminum and aluminum-zirconium compounds produced by the method of this invention typically comprise 10 to 60 weight percent solids, preferably 20 to 50 weight percent solids. Solutions which contain less than 10 weight percent solids can be produced however, they are not economically advantageous and are of little commercial value. The solids content of the solutions is determined on a theoretical basis and include the coordinated (bound) water that may be added with the reactants.

The final solutions can also have a wide range of metals:halide ratios. Typically the non-aqueous solutions of aluminum and aluminum-zirconium compounds produced by the method of this invention can have a metals:halide ratio of 0.33 to 2.0. Preferably the solutions should have a metals:halide ratio of 0.75 to 1.8.

The non-aqueous solutions of aluminum-zirconium compounds can be produced having a wide range of aluminum:zirconium ratios. Typically the non-aqueous solutions of aluminum-zirconium compounds have an Al:Zr ratio of 0.75 to 20. Preferably the solutions should have a Al:Zr ratio of 1.5 to 4.5.

The non-aqueous mediums useful in the instant invention are hydroxylated solvents including, but not limited to, alcohols, polyhydroxy alkyl compounds, polyhydroxy ethers, polyalkylene glycols, and polyalkylene ethers. The alcohols useful in the instant invention may be exemplified by, but not limited to methanol, ethanol and isopropanol. The polyhydroxy alkyl compounds useful in the instant invention may be exemplified by, but not limited to diols such as ethylene glycol, propylene glycol, 1,4-butanediol and 2-methyl 2,4-pentanediol; and triols such as glycerol, 1,2,4-hexanetriol, and 1,2,4-butanetriol. The polyhydroxy ethers useful in the instant invention may be exemplified by, but not limited to diethylene glycol, dipropylene glycol, triethylene glycol, tetraethylene glycol, diethylene glycol monomethyl ether, and diethylene glycol monoethyl ether. The polyalkylene glycols useful in the instant invention may be exemplified by, but not limited to, polyethylene glycols of the formula $H(OCH_2CH_2)_nOH$ where n is greater than 4 and less than 14. The polyalkylene ethers useful in the instant invention may be exemplified by, but not limited to, diethylene glycol dimethyl ether, diethylene glycol diethyl ether, and polyethylene ethers of the formula $R(OCH_2CH_2)_nOR$ where R is an alkyl group having 1 to 4 carbon atoms. Ethanol and propylene glycol are the preferred hydroxylated solvents useful in the instant invention.

It is preferred that the hydroxylated solvent be free of water but is not necessary that they be completely free of water. For example, 95% ethanol is useful in the instant invention.

The non-aqueous solutions of aluminum and aluminum-zirconium compounds may undergo additional processing following their formation. For example the solutions may be filtered to remove solid particulates. Or, the solutions can be distilled to remove water or other contaminants that may have been introduced with the hydroxylated solvent or the reactants. It is preferred to distill under vacuum thereby eliminating the need for high temperatures.

It should be understood by one skilled in the art that the formulas used herein to describe the various aluminum and aluminum-zirconium compounds and their raw material components are simplified and are intended to represent and include compounds containing coordinated and/or bound molecules of water as well as polymers, complexes and mixtures of the basic formula.

The components used in the method of the instant invention are commercially available or may be produced by known methods. For example aluminum chloride, $AlCl_3$ can be purchased from Aldrich Chemical Company as Aluminum chloride hexahydrate, $AlCl_3 \cdot 6H_2O$. Or aluminum chloride can produced by reacting aluminum metal and an organic acid, such as HCl. Zirconium oxychloride, $ZrOCl_2$, can be purchased from Dastech International, Inc. as zirconium oxychloride, $ZrOCl_2 \cdot 8H_2O$. Aluminum chlorohydrate is readily available. For example DOW CORNING ACH-323, DOW CORNING ACH-331, and DOW CORNING AACH-7171, Dow Corning Corp., Midland, Mich., are useful in the instant invention. Methods for producing aluminum chlorohydrate are also well known in the art.

The non-aqueous solutions of aluminum and aluminum-zirconium compounds are useful in antiperspirant compositions such as stick, roll-on, aerosol and pump sprays.

So that those skilled in the art can understand and appreciate the invention taught herein, the following examples are presented, being it understood that these examples should not be used to limit the scope of this invention over the limitations found in the claims attached hereto.

The solids, given below were determined on a theoretical basis and include the coordinated water that may be added with the reactants. The equipment used in the experiments included a 1000 ml, 3-necked round bottom flask equipped with an agitator, thermometer and a water cooled reflux condensor.

EXAMPLE 1

20.6 grams of $AlCl_3 \cdot 6H_2O$ was dissolved in 400.1 grams of 190 proof ethanol with agitation. A clear solution resulted. Aluminum chlorohydrate (Al=23%, Cl=15.16%, Al/Cl=1.99) was slowly added with agitation in increments of 20.0 grams until the total aluminum chlorohydrate added was 76.4 grams. It took approximately 2 days to complete the addition. The final solution was a pale yellow solution containing 20% (solids) of aluminum chlorohydrate and an Al/Cl ratio of 1.2:1. The experiment was conducted at room temperature and atmospheric pressure.

Another solution was prepared by dissolving 76.1 grams of $AlCl_3 \cdot 6H_2O$ in 350.00 grams of 190 proof ethanol. A clear solution resulted. A total of 73.9 grams of aluminum chlorohydrate (Al=23%, Cl=15.16%, Al/Cl=1.99) was added in increments of 10.0 grams approximately every hour. A slight viscosity increase was noted as the aluminum chlorohydrate was added. The final solution was a pale yellow solution containing 30% (solids) of aluminum chlorohydrate and an Al/Cl ratio of 0.75:1. The experiment was conducted at room temperature and atmospheric pressure.

EXAMPLE 2

61.1 grams of $ZrOCl_2 \cdot 8H_2O$ was dissolved in 350.9 grams of 190 proof ethanol. A clear solution resulted. To this, 88.9 grams of aluminum chlorohydrate (Al/Cl=1.99) was slowly added over an 8 hour period in increments of 20.0 grams. The final solution was a very pale white/yellow solution containing 30% (solids) of aluminum-zirconium chlorohydrate and a theoretical Al/Zr molar ratio of 4:1. The experiment was conducted at room temperature and atmospheric pressure.

An attempt was made to produce a solution containing 30% (solids) of aluminum-zirconium chlorohydrate and having a theoretical Al/Zr molar ratio of 0.5:1. 211.5 grams of $ZrOCl_2.8H_2O$ was dissolved in 250.3 grams of 190 proof ethanol. The mixture was heated to a temperature of 40° to 60° C. to dissolve the acid in the ethanol. At a temperature of 70° C. 28.2 grams of aluminum chlorohydrate (Al=23%, Cl=15.16%, Al/Cl=1.99) was slowly added in 5 to 10 gram increments. When the heat was removed a gel resulted.

EXAMPLE 3

35.4 grams of $AlCl_3.6H_2O$ was dissolved in 350.1 grams of propylene glycol with agitation. A clear solution resulted. Aluminum chlorohydrate (Al=23%, Cl=15.16%, Al/Cl=1.99) was slowly added with agitation in increments of 20.0 grams until the total aluminum chlorohydrate added was 114.6 grams. The final solution was a clear pale yellow solution containing 30% (solids) of aluminum chlorohydrate and an Al/Cl ratio of 1.2:1. The experiment was conducted at room temperature and atmospheric pressure.

EXAMPLE 4

1,018.4 grams of $ZrOCl_2.8H_2O$ was dissolved in 2,500 grams of propylene glycol. To this, 1,481.7 grams of aluminum chlorohydrate (Al/Cl=1.99) was slowly added in increments of approximately 300.0 grams every half hour until the reaction was complete. The final solution was a pale yellow solution containing 50% (solids) of aluminum-zirconium chlorohydrate and a theoretical Al/Zr molar ratio of 4:1 and a theoretical Al/Cl ratio of 1:1. The experiment was conducted at room temperature and atmospheric pressure.

EXAMPLE 5

10.8 grams of concentrated HCl was dissolved in 350.0 grams of 190 proof ethanol with agitation. A clear solution resulted. Aluminum chlorohydrate (Al=23%, Cl=15.16%, Al/Cl=1.99) was slowly added with agitation in 10 to 20 gram increments until the total aluminum chlorohydrate added was 139.2 grams. Sufficient time was allowed for the solution to again become clear between the additions of aluminum chlorohydrate. The final solution was a clear solution containing 30% (solids) of aluminum chlorohydrate and an Al/Cl ratio of 1.33:1. The experiment was conducted at room temperature and atmospheric pressure.

EXAMPLE 6

10.8 grams of concentrated HCl was dissolved in 350.2 grams of propylene glycol with agitation. A clear solution resulted. Aluminum chlorohydrate (Al=23%, Cl=15.16%, Al/Cl=1.99) was slowly added with agitation in 30 gram increments until the total aluminum chlorohydrate added was 139.2 grams. The final solution was a clear yellow solution containing 30% (solids) of aluminum chlorohydrate and an Al/Cl ratio of 1.33:1. The experiment was conducted at room temperature and atmospheric pressure.

EXAMPLE 7

350 grams of polyethylene glycol (PEG-12) was heated until liquified (approximately 27° C.). 61.2 grams of $ZrOCl_2.8H_2O$ was dissolved in it. The solution turned white and the agitation was set at approx. 370 rpm's. The mixture is stirred for 2.5 hours. A total of 88.9 grams of aluminum chlorohydrate (Al/Cl=1.99) was slowly added in increments of 10 to 20.0 grams over a period of 4.5 hours. During the addition the solution temperature increased to 31° C. The final solution was a pale yellow viscous solution containing 30% (solids) of aluminum-zirconium chlorohydrate.

EXAMPLE 8

61.1 grams of $AlCl_3.6H_2O$ was dissolved in 350 grams of ethylene glycol at room temperature. To this, 88.9 grams of aluminum chlorohydrate (Al/Cl=1.99) was slowly added in two additions over a period of 4 hours. The final solution was a clear yellow solution containing 30% (solids) of aluminum chlorohydrate. The experiment was conducted at room temperature and atmospheric pressure.

EXAMPLE 9

3.5 grams of $AlCl_3.6H_2O$ was dissolved in 350.2 grams of 190 proof ethanol with agitation. A clear solution resulted. Next, 37.5 grams of $ZrOCl_2.8H_2O$ was added turning the solution white. After approximately 1 hour the solution turned clear. Aluminum chlorohydrate (Al=23%, Cl=15.16%, Al/Cl=1.99) was slowly added with agitation in increments of 20 to 30 grams until the total aluminum chlorohydrate added was 109.0 grams. Sufficient time was allowed for the solution to become clear inbetween additions of aluminum chlorohydrate. It took approximately 8 hours to complete the addition. The final solution was a clear solution containing 30% (solids) of aluminum-zirconium chlorohydrate having an Al/Cl ratio of 1.27:1 and an Al/Zr ratio of 4:1. The experiment was conducted at room temperature and atmospheric pressure.

EXAMPLE 10

46.8 grams of Zr(OH)Cl (44.13% Zr, 25.16 Cl) was dissolved in 350.7 grams of 190 proof ethanol in 10 to 15 gram increments. A clear solution resulted. To this, 103.1 grams of aluminum chlorohydrate (23% Al, 15.16% Cl, Al/Cl=1.99) was slowly added in increments of 5 to 10 grams. The final solution was a white viscous solution containing 30% (solids) of aluminum-zirconium chlorohydrate and having a theoretical Al/Zr molar ratio of 3:1 and a theoretical Al/Cl molar ratio of 1.2:1. The experiment was conducted at room temperature and atmospheric pressure.

EXAMPLE 11

61.1 grams of $ZrOCl_2.8H_2O$ was dissolved in 350.6 grams of propylene glycol. To this, 88.9 grams of activated aluminum chlorohydrate was slowly added over an 8 hour period in increments of 20 to 30 grams. The final solution was a yellowish solution containing 30% (solids) of aluminum-zirconium chlorohydrate and a theoretical Al/Zr molar ratio of 4:1. The experiment was conducted at room temperature and atmospheric pressure.

What is claimed is:

1. A method of preparing non-aqueous solutions of aluminum and aluminum zirconium compounds wherein the method comprises
   A) protonating a hydroxylated solvent selected from the group consisting of alcohols, polyhydroxy alkyl compounds, polyhydroxy ethers, polyalkylene glycols, and polyalkylene ethers; by adding an acid selected from the group consisting of $ZrOCl_2$, $ZrO(OH)Cl$, $ZrCl_4$, $AlCl_3$, HCl, HI, HBr, $HNO_3$ and mixtures thereof to the hydroxylated solvent; and B) adding at a controlled rate to the protonated solvent aluminum chlorohydrate, $Al_2(OH)_aCl_{6-a}$, wherein a has the value of greater than 0 but less than 6; until the desired solution is formed.

2. A method as claimed in claim 1 wherein the acid is $ZrOCl_2$.

3. A method as claimed in claim 1 wherein the acid is $AlCl_3$.

4. A method as claimed in claim 1 wherein the acid is HCl.

5. A method as claimed in claim 1 wherein the hydroxylated solvent is ethanol.

6. A method as claimed in claim 1 wherein the hydroxylated solvent is propylene glycol.

7. A method as claimed in claim 1 wherein the hydroxylated solvent is a polyethylene glycol.

8. A method as claimed in claim 1 wherein heat is applied at step A.

9. A method as claimed in claim 1 wherein heat is applied at step B.

10. A method as claimed in claim 1 wherein heat is applied at steps A and B.

11. A method as claimed in claim 1 wherein the acid and aluminum chlorohydrate are in such quantities to produce an aluminum compound having a metals:halide ratio of 0.75 to 1.8.

12. A method as claimed in claim 1 wherein the acid and aluminum chlorohydrate are in such quantities to produce an aluminum-zirconium compound having a metals:halide ratio of 0.75 to 1.8.

13. A method as claimed in claim 1 wherein the acid and aluminum chlorohydrate are in such quantities to produce an aluminum-zirconium compound having a aluminum:zirconium ratio of 1.5 to 4.5.

14. A method as claimed in claim 1 wherein the solids content of the desired solution is 10 to 50 weight percent.

* * * * *